United States Patent [19]
Boeke et al.

[11] Patent Number: 5,830,751
[45] Date of Patent: Nov. 3, 1998

[54] GENETIC ASSAYS AND STRAINS USING HUMAN TP53

[75] Inventors: Jef D. Boeke; Rainer K. Brachmann, both of Baltimore, Md.

[73] Assignee: The Johns Hopkins University, Baltimore, Md.

[21] Appl. No.: 650,125

[22] Filed: May 1, 1996

[51] Int. Cl.[6] .............................. C12N 1/14; C07H 17/00
[52] U.S. Cl. .................................. 435/254.2; 435/320.1; 536/23.1; 536/23.4
[58] Field of Search ................................ 435/254.2, 69.1, 435/320.1; 536/23.1, 2, 23.4

[56] References Cited

PUBLICATIONS

Le Dourain et al., "A New Version of the Two–Hybrid Assay for Detection of Protein–Protein Interactions", *Nucleic Acids Research* 23(5):876–878 (1995).
Pierrat et al., "Functional Analysis of the Human Estrogen Receptor Using a Phenotypic Transactivation Assay in Yeast", *Gene* 119:237–245 (1992).
Saluz et al., "Approaches to Chracterize Protein–DNA Interactions In Vivo", *Critical Review in Eukaryotic Gene Expression* 3(1):1–29 (1993).
Brachmann, et al., "Dominant–negative p53 Mutations Selected in Yeast Hit Cancer Hot Spots", *Proc. Natl. Acad. Sci. USA*, vol. 93, pp. 4091–4095 (Apr. 1995).
Cho, Y. et al., "Crystal structure of p53 tumor suppressor–DNA complex: Understanding Tumorigenic mutations" Science 15 Jul. 1994. vol. 265 pp. 346–355.
Hollstein, M. et al. "Database of p53 gene somatic mutations in human tumors and cell lines" Nucleic Acids Research 1994, vol. 22, No. 17, pp. 3551–3555.
Lasky, T. et al. "p53 mutations associated with breast, colorectal, liver, lung, and ovarian cancers" Environmental Health Perspectives Dec. 1996 vol. 104, No. 12. pp. 1324–1331.
Park et al. 1994 Oncogene 9(7):1899–1906.

*Primary Examiner*—Karen Cochrane Carlson
*Attorney, Agent, or Firm*—Banner & Witcoff, Ltd.

[57] ABSTRACT

Yeast strains carrying a human wild-type TP53 are employed to select for mutations. The types of mutations can be analyzed genetically as recessive or dominant-negative. The mutational spectrum of dominant-negative TP53 mutants selected in yeast correlates tightly with TP53 mutations found in human cancers. Thus the use of such yeast assays is validated for studying the effects of various agents on human TP53, one of the most important and ubiquitous of human cancer genes. Assays, kits, and constructs are provide which use yeast as a genetic system for making and studying human TP53 mutations. Such assays can be used to develop therapeutic agents, to study putative carcinogens, and to identify other cellular components which interact with p53 and abrogate its activity.

12 Claims, 2 Drawing Sheets

FIG. 2

| Hot spot regions | Codon | wild-type amino acid | mutant amino acid | | | |
|---|---|---|---|---|---|---|
| | 127 | Ser | Pro | | | |
| 132<br>\|<br>143 | 132 | Lys | Asn | | | |
| | 135 | Cys | Phe | | | |
| 151<br>\|<br>159 | 151 | Pro | His | Arg | | |
| | 158 | Arg | Pro | | | |
| 172<br>\|<br>179 | 176 | Cys | Arg | | | |
| | 179 | His | Asn | | | |
| | 236 | Tyr | Asp | | | |
| 237<br>\|<br>249 | 241 | Ser | Phe | | | |
| | 242 | Cys | Phe | | | |
| | 244 | Gly | Asp | Ser | | |
| | 245 | Gly | Ser | Arg | Ser | Ser | Asp |
| | 246 | Met | Arg | Ile | | |
| | 248 | Arg | Trp | Trp | | |
| | 252 | Leu | Thr | Thr | | |
| | 257 | Leu | Pro | Gln | | |
| | 259 | Asp | Tyr | | | |
| | 265 | Leu | Pro | | | |
| 272<br>\|<br>286 | 273 | Arg | Pro | Pro | | |
| | 277 | Cys | Tyr | | | |
| | 278 | Pro | His | Ser | | |
| | 279 | Gly | Glu | Glu | Glu | |
| | 280 | Arg | Ser | Thr | | |
| | 281 | Asp | Gly | Tyr | Gly | |

5,830,751

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AATTTAGGCA TGTCTAGGCA TGTCTA        2 6

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATTTAGACA TGCCTAGACA TGCCTA        2 6

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GAAGGTTAAT GTGGCTGTGG TTTCAGGGTC CATAAAGCTT GTCCTGGAAG TCTCATGGAG        6 0

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCAGGATCCC TAGGTTCCTT TGTTACTTCT TCCG        3 4

( 2 ) INFORMATION FOR SEQ ID NO:5:

( i ) SEQUENCE CHARACTERISTICS:
        ( A ) LENGTH: 18 base pairs
        ( B ) TYPE: nucleic acid ( C ) STRANDEDNESS: single
            ( D ) TOPOLOGY: linear ( x i ) SEQUENCE DESCRIPTION: SEQ ID NO:5:

ACCAGCAGCT CCTACACC                                                                                      18

( 2 ) INFORMATION FOR SEQ ID NO:6:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

GAGGAGCTGG TGTTGTTG                                                                                      18

( 2 ) INFORMATION FOR SEQ ID NO:7:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

CCATCCTCAC CATCATCAC                                                                                     19

( 2 ) INFORMATION FOR SEQ ID NO:8:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:8:

GCAGGGGAGG GAGAGATGG                                                                                     19

GENETIC ASSAYS AND STRAINS USING HUMAN TP53

The U.S. Government has a paid-up license in this invention and the right in limited circumstances to require the patent owner to license others on reasonable terms as provided for by the terms of grants awarded by the National Institutes of Health.

BACKGROUND OF THE INVENTION

More than half of all human cancers are associated with one or more alterations in the tumor suppressor gene TP53 (1–4). Many premalignant lesions, a subset of malignant clones, and germlines of families prone to cancer are characterized by the presence of one wild-type and one mutant allele of TP53 (5–9). In this situation the mutant p53 protein may act in a dominant-negative fashion, ultimately leading to loss of heterozygosity and thus a further growth advantage for the malignant cells. Alternatively, the mutant p53 protein may have acquired a new tumor promoting activity which is independent of wild-type p53. These hypotheses are based on the analysis of only a few TP53 mutations usually in the setting of over-expression of the mutant protein, and their relevance to TP53 mutations in general has not been proven (8, 10–13).

There is a need in the art for additional systems in which to study mutations in human p53, an important and ubiquitous cancer suppressor gene.

SUMMARY OF THE INVENTION

It is an object of the invention to provide a yeast cell useful for selecting and studying mutations in human p53.

It is another object of the invention to provide a method of identifying compensatory mutations in TP53 which suppress dominant-negative TP53 mutant phenotypes.

It is still another object of the invention to provide a method of identifying potential therapeutic agents.

It is yet another object of the invention to provide a method of screening putative carcinogens.

It is yet another object of the invention to provide a method for identifying cellular proteins which interact with p53 and abrogate its activity.

It is an object of the invention to provide a kit for isolating mutations in p53.

It is another object of the invention to provide a gene fusion useful for isolating and studying p53 mutations.

These and other objects of the invention are provided by one or more of the embodiments described below. In one embodiment of the invention a yeast cell is provided. The cell comprises a first reporter gene which is selectable or counterselectable. The reporter gene is operably linked to a DNA sequence to which human p53 specifically binds. The cell also comprises a first fusion gene which expresses a human p53 in the cell. The fusion gene comprises a promoter operably linked to a human p53 coding sequence.

In another embodiment of the invention a method of identifying compensatory mutations in TP53 which suppress dominant-negative TP53 mutant phenotypes is provided. The method involves providing a cell which comprises:

(i) a reporter gene which is selectable, wherein the reporter gene is operably linked to a DNA sequence to which human p53 specifically binds; and (ii) a first fusion gene which expresses a dominant-negative allele of human p53 in the cell, the fusion gene comprising a promoter operably linked to a human p53 coding sequence.

Then a population of DNA molecules comprising a second fusion gene is introduced into the cell. The second fusion gene comprises a promoter operably linked to a mutagenized human p53 coding sequence. Phenotypic revertants of the dominant-negative allele of human TP53 are selected using the selectable phenotype of the reporter gene.

According to another embodiment of the invention a method of identifying potential therapeutic agents is provided. A cell is provided which comprises:

a reporter gene which is selectable, wherein the reporter gene is operably linked to a DNA sequence to which human p53 specifically binds; and a fusion gene which expresses a dominant-negative allele of human TP53 in the cell, the fusion gene comprising a promoter operably linked to a human p53 coding sequence.

Test compounds are contacted with the cell. The selectable phenotype of the reporter gene is assayed. Desirable test compounds are identified as potential therapeutic agents if they induce the cell to display the selectable phenotype.

In another aspect of the invention a method of screening putative carcinogens for their effect on a p53 allele is provided. A cell is provided which comprises:

a reporter gene which is counterselectable, wherein the reporter gene is operably linked to a DNA sequence to which human p53 specifically binds; and a fusion gene which expresses human p53 in the cell, the fusion gene comprising a promoter operably linked to a human p53 coding sequence.

The cell is contacted with a putative carcinogen. Cells are isolated which contain a mutation in the human p53 coding sequence by counterselecting for loss of expression of the reporter gene.

According to another embodiment of the invention cellular proteins which interact with p53 and abrogate its activity are identified. A population of cells is provided which comprise:

a reporter gene which is counterselectable, wherein the reporter gene is operably linked to a DNA sequence to which human p53 specifically binds; and a fusion gene which expresses human p53 in the cell, the fusion gene comprising a promoter operably linked to a human p53 coding sequence.

A library of human cDNA molecules is introduced into the population of cells. Each of the cDNA molecules is operably linked to expression control sequences so that the human cDNA is expressed in the cell. The cells are assayed to identify those which express the counterselectable phenotype of the reporter gene. The counterselectable phenotype identifies cells which express a protein which abrogates p53 activity.

According to another aspect of the invention a kit is provided. The kit comprises three yeast strains. The first yeast strain comprises a centromeric plasmid which itself comprises: a fusion of a yeast alcohol dehydrogenase promoter operably linked to a human p53 coding sequence; and a yeast histidine (HIS3) gene. The first yeast strain also comprises an integrated reporter gene which consists of a p53 consensus binding sequence inserted upstream from the URA3 locus. The second yeast strain comprises an integrated reporter gene which consists of a p53 consensus binding sequence inserted upstream from the URA3 locus. The third yeast strain comprises a centromeric plasmid which itself comprises a fusion of a yeast alcohol dehydrogenase promoter operably linked to a human p53 coding sequence, and a yeast LEU2 gene. The third yeast strain also contains an integrated reporter gene which consists of a p53 consensus binding sequence inserted upstream from the URA3 locus. The first strain is of a compatible mating type to the second and third strains.

In still another embodiment of the invention a tripartite gene fusion is provided. The fusion comprises a human p53-specific DNA-binding site; a yeast URA3 gene; and a portion of a yeast SPO13 gene. The human p53-specific DNA-binding site is upstream of the URA3 gene, and the portion of the yeast SPO13 gene is interposed between the URA3 gene and the human p53-specific DNA-binding site. Moreover, the portion of the yeast SPO13 gene consists of the first 15 codons of SPO13 and nucleotides 5' to nucleotide −170.

These and other embodiments of the invention provide the art with tools for studying mutagenesis and carcinogenesis in general, as well as for studying the important cancer-related gene TP53.

BRIEF DESCRIPTION OF THE DRAWINGS

FIG. 2 Comparison of the dominant-negative ADH-p53 mutations selected in yeast to the five hotspot regions of human cancer mutations and to reported germline mutations (Li-Fraumeni syndrome and others). The boxed yeast mutations hit the hotspot regions (2, 5). For codons with shaded background germline mutations have been reported (7, 27, 28). The figure shows the clustering of the strongest dominant mutations to codons 179, 241–248 and 277–281. Mutations of class 1 are in bold and of class 2 in plain text.

DETAILED DESCRIPTION OF THE PREFERRED EMBODIMENTS

Figure 1:
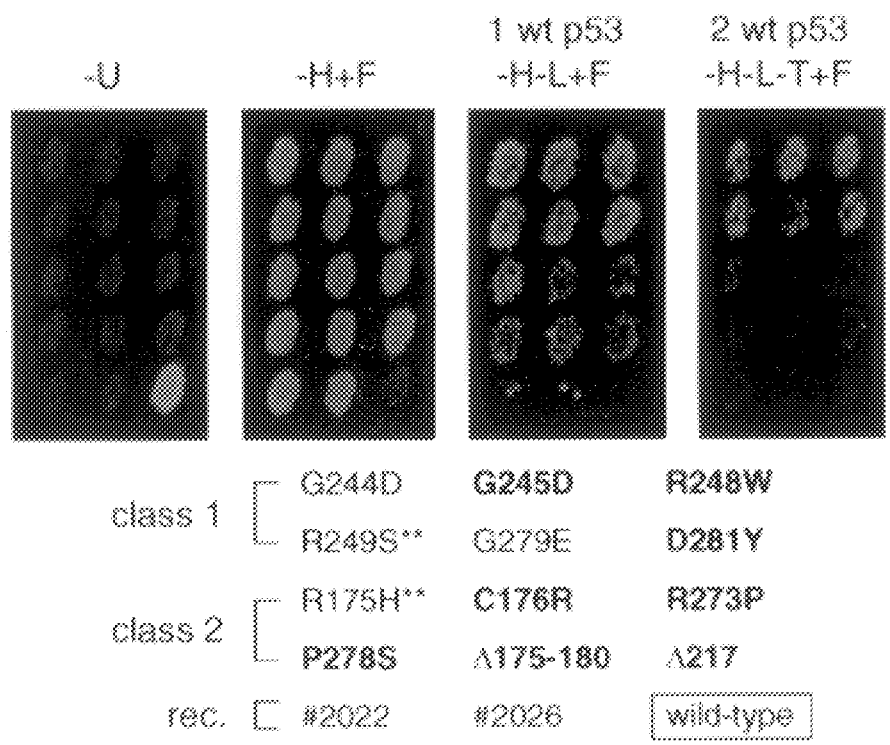
FIG. 1 Phenotypes of p53 mutants selected in yeast. In contrast to wild-type p53 (phenotype $Ura^+Foa^S$) all dominant-negative as well as recessive mutants are $Ura^-$ $Foa^R$. Upon mating to strains with one or two wild-type ADH-p53 expression vectors the dominant-negative mutants can be classified by their degree of dominance over wild-type p53. The stronger class 1 interferes with one and two copies of wild-type ADH-p53 and thus survives on Foa plates. The weaker class 2 is only dominant over one wild-type copy. For the p53 mutants in bold letters NcoI/StuI fragments with the mutations were recloned into the wild-type ADH-p53 plasmid pRB16. The mutants with ** represent hotspot codons which were not identified by our screen (1, 2, 4) (see Table 3). #2022 and #2026 are recessive mutations leading to the expression of truncated p53 proteins. The media used were SC −Ura (−U), SC −His +Foa (−H +F), SC−His −Leu +Foa (−H−L+F), and SC −His −Leu −Trp +Foa (−H−L−T+F). The −U and −H+F media test for p53 function (wild-type grows on −U and fails to grow on −H+F). The −H−L+F medium tests for the ability of mutant p53 to interfere with the function of a single wild-type copy of p53 (present on a LEU2 plasmid); dominant-negative mutants will grow on this medium. The −H−L−T+F medium tests for the ability of mutant p53 to interfere with the function of two wild-type copies of p53 (present on LEU2 and TRP1 plasmids).

We developed a yeast assay for p53 and its consensus DNA binding site to screen for and analyze spontaneous dominant-negative p53 mutations. We have discovered that such mutations cluster in the mutational hotspots of human cancers. We have demonstrated different degrees of dominance, the most dominant mutations localizing to codons 179, 241–248 and 277–281. These results are fully consistent with a dominant-negative mode of action for the large majority of tumorigenic TP53 alleles.

Our p53 assay is based on the principles of yeast systems designed by Fields and others, which allow the study of protein/protein interactions by simple phenotypic readouts (19–23). The use of a counterselectable marker, such as URA3, as the reporter gene, allows screening for and against p53 expression. In a preferred embodiment, activation of URA3 leads to survival on medium lacking uracil, but prevents growth on plates containing 5-fluoro-orotic acid (Foa) due to the conversion of Foa to a toxic product (resulting in a $Ura^+Foa^S$ phenotype) (24). In our assays, URA3 activation depends upon the site-specific binding of p53 to its consensus DNA binding site (25) placed upstream of URA3; p53 expression is driven by the ADH1 promoter from a CEN (centromeric) plasmid (ADH-p53), which is maintained at approximately one copy per cell.

Yeast cells are employed for the assays described here, although other cell types, both prokaryotic and eukaryotic, preferably with well defined genetics, can be used as well. Yeast are particularly useful because of their well-developed genetic system. Reporter genes useful according to the present invention are selectable or counterselectable, or both. The URA3 gene is particularly useful. Other useful counterselectable genes include LYS2, LYS5, CAN1, MET2, MET15, and GAL1. The reporter gene is operably linked to a DNA sequence to which human p53 specifically binds. An actual human p53-binding sequence or any sequence which conforms to the consensus sequence taught by el-Deiry (25) can be used. Among this family of sequences there may be a slight variation in the behavior in the assays. As shown by the actual p53-binding human sequences, slight variations from the consensus sequence can be made while still enabling p53 to specifically bind. Operable linkage, according to the present invention, means that the DNA sequence is upstream of the reporter gene and close enough so that p53 binding activates transcription of the reporter gene. Typically this is within about 1 kb.

It is desirable that at least one of the reporter gene constructs of the present invention be integrated in the genome. This can be accomplished readily by amplification of the construct and introduction into yeast by any technique known in the art. The transformed construct can integrate via homologous recombination at the site of the endogenous reporter gene or at any marker gene site. This event can be readily selected for if the genomic target site is mutated and the transforming marker gene is wild-type.

A fusion gene which expresses a human p53 in a yeast cell typically has p53 coding sequences linked to an endogenous yeast cell promoter. Useful promoters are those for "housekeeping" genes which are typically expressed throughout the life cycle at high levels. One such useful promoter is that for the alcohol dehydrogenase gene, but others may be used as is convenient. Promoters are operably linked to a TP53 gene when they drive transcription of the gene. Such promoters are usually upstream and within about 1 kb of the start of translation.

Suitable TP53 alleles for use in the various embodiments of the present invention are wild-type alleles as well as mutants. The mutant alleles may be those which are experimentally made, but more interesting alleles are those which are found in human cancers. Most interesting alleles are those which are dominant-negative, which means that the alleles cause a mutant phenotype even in the presence of a wild-type allele.

After generation of mutations in TP53 on a first expression plasmid it is often desirable to test the mutant allele in the presence of wild-type TP53. This can be accomplished by mating with a compatible haploid yeast strain which contains a wild-type TP53 expression construct. Preferably the two TP53 expression constructs will produce p53 at similar levels, or if not, at levels which can be manipulated, such as by controlled induction. The phenotype of the diploid cell containing a mutant and wild-type allele of TP53 can be assayed or observed, to determine whether the mutation is recessive or dominant.

In another aspect of the invention a second reporter gene is introduced into the yeast cell which contains a reporter gene as well as a fusion gene expressing p53. The second reporter gene can be selectable, counterselectable, or both. The reporter gene can be the same or different from the first reporter gene. Like the first reporter gene, the second reporter gene is operably linked to a DNA sequence to which human p53 specifically binds. This reporter gene allows one to determine whether a mutation occurred on the TP53-plasmid or on the genomic reporter gene.

The set of yeast strains and plasmids disclosed here lend themselves to a variety of methods. In one method, mutations which are able to compensate for a dominant-negative TP53 mutation are identified. Such compensatory mutations are of intrinsic scientific interest, to determine interactions between portions of the p53 multimer. In addition, a compensatory mutation which functions in trans to suppress a dominant-negative TP53 mutant phenotype will be useful in therapeutic applications. Such mutations will also be instructive in the design of drugs which have the same effect on dominant-negative p53 mutants. By using the strains described herein, one can, for example mutagenize human p53 coding sequences and introduce them to strains which contain a selectable reporter gene operably linked to a DNA sequence to which human p53 specifically binds, and a TP53 expression construct which has a dominant-negative mutation. Desirably the mutation will be one commonly found in human tumors. Using the selectable phenotype of the reporter gene, one can select for a change in phenotype due to the introduction of a particular mutagenized human p53 coding sequence.

According to another aspect of the invention, potential therapeutic agents can be identified. Using a cell according to the present invention which has a selectable reporter gene operably linked to a DNA sequence to which human p53 specifically binds and a fusion gene which expresses a dominant-negative allele of human TP53, one can perform a drug screening assay. Preferably the allele is one found in human tumors. Test compounds can be contacted with such cells and one can select for the ability of the cells to express the reporter gene. Candidate therapeutic agents are able to induce the cell to display the selectable phenotype of the reporter gene.

Another method for which the strains of the present invention are particularly suited is a screening assay for putative carcinogens. The Salmonella/mammalian-microsome mutagenicity test developed by Bruce Ames and co-workers has confirmed many carcinogens as mutagens and has identified numerous new mutagens. The test is based on a prokaryotic system with reporter genes which play no role in human carcinogenesis. A eukaryotic system which tests the mutagenicity of compounds on, for example, tumor suppressor genes aids in the classification of and risk assessment for mutagens/carcinogens.

For the tumor suppressor gene p53 there are several examples of mutagens which cause specific mutations in the p53 sequence. Theses include, amongst others, UV light leading to skin cancer and aflatoxin B1 leading to hepatomas. The causal relationships could only be demonstrated because of strong epidemiological data for exposure to a single or few mutagens and a high incidence of the cancer. Similar causal relationships may exist for other mutagens and cancers; however, they are more difficult to prove because there is concomitant exposure to various mutagens and a lower incidence of the specific cancer. A eukaryotic mutagenicity assay for the p53 gene enables the identification of mutagens that cause a specific pattern of p53 mutations.

Using a strain which has a counterselectable reporter gene operably linked to a DNA sequence to which human p53 specifically binds and a fusion gene which expresses human p53 in the cell, one can test putative carcinogens by contacting them with the cell. Using the counterselection, one can identify carcinogens which have induced mutations in TP53. If desired the particular mutations can be identified, for example, by sequencing. Thus particular mutational fingerprints on TP53 of the carcinogens can be identified. Such fingerprints can be used epidemiologically, for example to assess the effects of particular carcinogens on populations.

If desired, one can incubate putative carcinogens with a mammalian liver lysate prior to the incubation with the tester cells. Such liver lysates are able to metabolize pre-carcinogens to carcinogens, as occurs in the human or animal body.

The assay can be performed, for example, using a yeast strain which is homozygous diploid for the reporter gene UAS53::URA3 and which contains a single copy of wild-type p53 on a centromeric plasmid. Known mutagens, such as UV light, aflatoxin B1 and benzo[α]pyrene, or unknown mutagens are applied to the yeast cells. Mutations which cause a non-functional p53 protein lead to a phenotype change from $Ura^+Foa^S$ to $Ura^-Foa^R$ which can be easily screened for. Based on our experience with the system, other mutations can also lead to Foa resistance, most of which are recessive mutations in the UAS53::URA3 reporter gene. By using a strain which is homozygous diploid for the reporter gene the frequency of these mutations will be reduced to $1\times10^{-6}$ and should therefore be negligible. In addition, a second wild-type p53 expression construct can be integrated into the genome. Thus the assay will preferentially identify dominant-negative p53 mutations. The plasmids with the mutated p53 genes can be recovered from yeast, expressed in E. coli, purified, and sequenced.

The yeast assay for carcinogenic compounds can be performed in the following way:

1. Homozygous diploid UAS53::URA3 yeast cells which are His⁻ and which bear an episomal p53 expression plasmid with a HIS3 marker gene are plated as a lawn onto −His plates.

2. Crystals, impregnated filter paper disks, or droplets of the compound(s) to be tested are applied to the lawn, setting up a gradient of the compound as the test cells grow. If the test compound has strong mutagenic potential, p53 mutants arise at higher frequencies in the zones containing higher concentrations of the compound.

3. The lawn of cells is transferred, by replica-plating, to a −His plate containing 5-Foa, selecting for the p53 plasmid. Only p53 mutants should grow on these plates. Mutagenic effect on p53 is observed as a halo of Foa-resistant colonies surrounding the spot at which the compounds were originally placed.

4. The plasmids bearing p53 mutations are recovered from the yeast colonies. The nature of the mutation(s) can be determined by DNA sequencing.

Note that step 1 can be performed, as in the Ames test, by the inclusion of a rat liver homogenate on the plate, providing the enzymes (mixed function oxygenases, cytochrome P-450s, etc.) that can activate certain precarcinogens to carcinogens. Furthermore, yeast strains with mutations in important DNA repair enzymes can be used in order to increase the sensitivity of the test.

Because our system is yeast-based there are two ways in which p53 mutagenesis may be different from mutagenesis in human cells. i) There is no DNA methylation in yeast. Thus mutagens which affect methylated bases will not be active in the assay. This can be overcome (if necessary) by expression of the appropriate methyltransferase(s) in yeast. ii) p53 cDNA lacks introns, thus mutations at splice junctions will not be represented. These are known, however, to be very rare events based on the sequence information of p53 mutations in human cancers. Additionally, some compounds may not be able to enter the yeast cells because of their cell walls. This can be circumvented by the preparation and use of spheroplasts or by the utilization of yeast strains with mutations which affect cell permeability.

The strains of the present invention also lend themselves to methods for identification of other cellular components which interact with p53, either stimulating or inhibiting its binding to its specific binding sequences. Using a counterselectable reporter gene and a TP53 expression construct, one can introduce a library of human cDNA molecules each of which is operably linked to expression control sequences. Selecting against the reporter gene using a counterselective agent, e.g., 5-FOA in the case of URA3, identifies individual clones which contain a human cDNA which inhibits p53 activity, possibly by means of the protein which the cDNA encodes.

This method was tested in a pilot study. A reporter strain (UAS53::URA3/p53) was transformed with exon 2 of the SV40 large T antigen (TAg), a viral antigen known to prevent DNA binding and transactivation by p53. The large T antigen plasmid pGAD-T2 was originally designed for a two-hybrid screen and encodes a Gal4 transactivation domain-TAg fusion. The large T antigen fusion protein was able to interfere with p53 activity in our system, changing the phenotype from Foa$^S$ to Foa$^R$, while the control vector plasmid pGAD-2F encoding the Gal4 transactivation domain alone was unable to do so.

Kits are also contemplated as part of the invention which comprise useful sets of yeast strains and/or plasmids. In one contemplated kit, three strains are provided. A first yeast strain contains a centromeric plasmid. The plasmid contains a gene fusion of a yeast alcohol dehydrogenase promoter operably linked to a human p53 coding sequence; and a yeast histidine (HIS3) gene. The first yeast strain also contains an integrated reporter gene which consists of a p53 consensus binding sequence inserted upstream from the URA3 locus. This strain can be used for selection of TP53 mutants. The other two strains can be used for genetic characterization of the TP53 mutants which are isolated. The second yeast strain contains an integrated reporter gene which consists of a p53 consensus binding sequence inserted upstream from the URA3 locus, within a distance short enough so that binding of p53 activates URA3 transcription. The third yeast strain contains a centromeric plasmid which contains a fusion of a yeast alcohol dehydrogenase promoter operably linked to a human p53 coding sequence, and a yeast LEU2 gene. The third yeast strain also contains an integrated reporter gene which consists of a p53 consensus binding sequence inserted upstream from the URA3 locus. The first strain is of a compatible mating type to the second and third strains, such that the first strain can be mated with each of the others to form diploid cells. Examples of each of these strains are provided in Table 1. Uses of these strains are discussed throughout. Written instructions for performing any of the assays described herein may also be enclosed in the kit, as well as media and selective agents. Strains are typically packaged separately and then bundled or held together in a common container.

Also provided by the present invention is a tripartite gene fusion suitable for integration into the yeast genome. The gene fusion contains a human p53-specific DNA-binding site, a yeast URA3 gene, and a portion of a yeast SPO13 gene. The human p53-specific DNA-binding site is upstream of the URA3 gene, and the portion of the yeast SPO13 gene is interposed between the URA3 gene and the human p53-specific DNA-binding site. The portion of the yeast SPO13 gene consists of the first 15 codons of SPO13 and nucleotides upstream thereof, until nucleotide −170. Importantly, the SPO13 upstream region contains a URS (upstream repressing sequence) that prevents basal low level transcription of URA3. Such a construct is disclosed in detail below, and can be used in formation of strains useful for the practice of the disclosed methods.

The following examples are provided for exemplification purposes only and are not intended to limit the scope of the invention.

EXAMPLES

Example 1: Yeast Strains, Plasmids and Isolation of TP53 Mutants.

All of the yeast media used here (e.g. −His) were dropout media based on synthetic complete supplemented minimal medium (14) lacking the indicated nutrient(s). The yeast strains and plasmids used are described in Table 1.

TABLE 1

| Yeast strains | | |
|---|---|---|
| Strain | Relevant genotype* | Plasmids (markers)† |
| RBy33 | MATα 1cUAS53::URA3 | — |
| RBy41 | MATα 1cUAS53::URA3 | pRB16 (ADH-p53 HIS3 CEN) |
| RBy159 | MATα 1cUAS53::URA3 | — |
| RBy160 | MATα 1cUAS53::URA3 | pLS76 (ADH-p53 LEU2 CEN) |
| RBy161 | MATα 1cUAS53::URA3 | pLS76 (ADH-p53 LEU2 CEN) |
| | | pRB17 (ADH-p53 TRP1 CEN) |
| RBy162 | MATα ura3-52 | pLS76 (ADH-p53 LEU2 CEN) |

*All strains listed (except RBy162) are also lys2Δ202 trp1Δ63 his3Δ200 leu2Δ1. RBy162 is also lys2Δ202 trp1Δ63 his3Δ200 leu2Δ1 ade2Δ.
†pRB16 and pRB17 were derived from pLS76 (15) by subcloning the XhoI-SacI fragment containing ADH-p53 (including the CYC1 transcription terminator) into CEN vectors pRS413 and pRS414 (16), respectively.

Construction of Reporter Gene

We fused the SPO13 promoter to a sequence encoding a fusion protein with the first 15 amino acids of SPO13 and the URA3 protein (SPO13::URA3 in pPL128). The SPO13::URA3 fragment was excised from pPL128 and cloned into a pBSK plasmid (Stratagene). The resulting plasmid, pMV252, contains EcoRI sites at −170 and −368 in the SPO13 promoter.

For construction of the UAS53::URA3 reporter genes, oligonucleotides corresponding to the p53 consensus DNA binding site (JB820:5'-AATTTAGGCATGTCTAGGCATGTCTA-3' (SEQ ID NO: 1) and JB821:5'-AATTTAGACATGCCTAGACATGCCTA-3' (SEQ ID NO: 2) (14) were annealed, phosphorylated, and ligated into EcoRI-digested pMV252.

The UAS53::URA3 alleles were integrated at the ura3-52 locus by homologous recombination of the product of a PCR reaction. The 5' primer used was JB516 that contains 40 nucleotides of the URA3 sequence upstream of its promoter (−257 to −218) fused to 20 nucleotides of the SPO13 promoter (−370 to −351 (11):5'-GAAGGTTAATGTGGCTGTGGTIT-CAGGGTCCATAAAGCTTGTCCTGGAAGTCTCA TGGAG-3' (SEQ ID NO: 3). The 3' primer used was 3'URA3 (URA3 sequence +656 to +632 (12)):5'-TCAGGATCCCTAGGTTCCTTTGTTACTTCTTCCG-3' (SEQ ID NO: 4).

Isolation of Independent TP53 Mutations

For isolation of independent TP53 mutations, patches of single colonies from RBy41 (containing an ADH-p53 HIS3 expression vector (pRB16) and the integrated reporter gene 1cUAS53::URA3) were grown on synthetic complete medium without histidine (SC −His plates), replica-plated to SC −His +0.15% 5-fluoro-orotic acid (Foa) plates and incubated for 2 to 4 days at 37° C. until 5-fluoro-orotic acid resistant (Foa$^R$) papillae emerged.

Only one single Foa$^R$ colony was isolated from each parental patch. These Foa$^R$ clones were 1) mated to RBy159 (MATα, isogenic to RBy41, but lacking an ADH-p53 expression vector) and replica-plated to SC −Ura plates and 2) mated to RBy160 (RBy159 with the ADH-p53 LEU2 plasmid pLS76 (15)) followed by replica-plating to SC −His −Leu plates to select for diploids and then SC −His −Leu +0.15% Foa plates to evaluate the dominance/recessivity of the Foa$^R$ phenotype. Clones which were Ura$^+$ in mating assay #1 and Foa$^S$ in assay #2 were recessive and were not due to TP53 plasmid-dependent mutations. Most of these clones represent recessive mutations that knock out 1cUAS53::URA3. Clones which were Ura$^-$ in assay #1 and Foa$^S$ in assay #2 were TP53 plasmid-dependent recessive mutations. Only clones which were Foa$^R$ in assay #2 potentially contained a dominant-negative TP53 plasmid-dependent mutation; these were further characterized by growing them non-selectively and isolating strains which had lost the (potentially mutated) pRB16. A wild-type TP53 expression plasmid was then introduced into these strains as follows. The plasmid-free strains were mated to RBy162 (MATαura3-52 and containing pLS76), replica-plated to SC −Ade −Leu plates to select for diploids, followed by replica-plating of the diploids to SC −Leu +0.15% Foa plates. Foa$^R$ clones which regained their Foa$^S$ phenotype as a result of these manipulations were judged to contain dominant-negative TP53 plasmid-dependent mutations.

Example 2: Identification and Classification of Dominant-Negative TP53 Mutants

We isolated a total of 49 independent spontaneous p53 mutants that behaved in a dominant-negative fashion. These mutants were identified using a two-step selection procedure. In the first step, haploid yeast colonies deficient in URA3 expression were selected on plates containing Foa. In the second step, these colonies were mated to strains containing either the wild-type reporter gene or one copy of wild-type ADH-p53 and subsequently transferred to plates containing Foa. Dominant-negative alleles of TP53 showed an Foa$^R$ phenotype in both cases. Recessive alleles of TP53 or cis-acting reporter-linked mutations exhibited an Foa$^S$ phenotype in the presence of an additional copy of wild-type ADH-p53 or the wild-type reporter gene, respectively.

Characterization of TP53 mutants

The mutant pRB16 plasmids from all identified dominant-negative TP53 plasmid dependent clones were recovered in bacteria (17), retransformed into RBy33 (RBy41 without pRB16) and the phenotypes rechecked. The dominant-negative phenotypes were then further classified by testing the degree of the dominance over one or two doses of wild-type ADH-p53 as follows. The retransformed strains bearing mutant pRB16 derivatives were mated to RBy160 and RBy161 (RBy159 containing two ADH-p53 expression plasmids, pLS76 (15) and pRB17, which is identical to pRB16 except for the selectable marker TRP1 (16)), replica-plating them to SC—His—Leu and SC −His −Leu −Trp plates respectively, replica-plating them to the same selective plates with 0.15% Foa and incubating them at 30° C. for 2 to 4 days.

Some of the dominant-negative TP53 mutants were isolated as false positives from a cDNA library screen that is irrelevant to this invention; these mutants were characterized in the same fashion (Table 2). Due to the fact that this subset of the mutants studied did not necessarily represent independent isolates, a numerical analysis of mutation frequencies within this subset would be meaningless.

The recessive plasmid-dependent TP53 mutants were also recovered into bacteria and retransformed. These isolates (as well as the dominant isolates) were evaluated by immunoblotting with anti-p53 antibody PAb 1801, performed as described. RBy50 (pRS413 (16) in RBy33) was used as the negative control.

TABLE 2

| Properties of independent TP53 mutations selected in yeast | |
|---|---|
| Total number of Foa$^R$ clones | 717 |
| Number of TP53 plasmid-dependent mutants | 111* |
| Recessive mutants | 67 (9%) |
| Dominant mutants | 31 (4%)† |
| class 1 | 13 |
| class 2 | 18 |

*13 plasmid-dependent mutants could not be classified, since they did not show consistent phenotypes before and after plasmid recovery and retransformation.
†18 additional independent dominant-negative mutants were obtained as false positives in a cDNA library screen. These mutants are independent by virtue of a unique mutation and are identified by * in Table 3.

Recessive mutations in the reporter gene were found in 87% and in the TP53 gene in 9% of all mutants. 4% of the Foa$^R$ colonies contained dominant-negative TP53 mutations (Table 2). Once the dominant-negative TP53 mutants had been identified, the TP53 plasmids were recovered and transformed into a fresh reporter strain (RBy33) to exclude artifacts of the original strain. In all cases the same dominant-negative phenotype could be reproduced. The dominant-negative mutants could be further classified by mating them to a strain with two wild-type ADH-p53 plasmids thus characterizing the dominance of the mutant proteins in the presence of two doses of the wild-type ADH-p53 gene. The most dominant mutants were able to interfere with one and two copies of wild-type ADH-p53 (class 1). Less dominant TP53 mutants could only override the activity of a single wild-type allele (class 2) (FIG. 1). These classes represented 43% and 57% of the dominant-negative TP53 mutants, respectively.

Example 3: Sequences of the Dominant-Negative TP53 Mutants

We then sequenced the core domains (codons 102–292) of the 49 dominant-negative mutants.

Miniprep DNA (17) for the plasmids was RNase treated (7 mg/ml, 10 min, 37° C.), extracted with phenol/chloroform and sequenced with Taq polymerase (Perkin-Elmer) using Prizm kit dye-terminator cycle sequencing on an Applied Biosystems 373A Stretch automated sequencer. Sequences were analyzed using Sequencher software (Gene Codes Corporation, Inc., Ann Arbor, Mich.) for the Macintosh. The core domains of ADH-p53 were sequenced using primers JB990 (5'-ACCAGCAGCTCCTACACC-3') (SEQ ID NO: 5) and JB991 (5'-GAGGAGCTGGTGTTGTTG-3') (SEQ ID NO: 6). Eight dominant-negative clones (bold numbers in Table 3) were further analyzed by ligating NcoI/StuI fragments with the mutations (base pairs 477 to 1039) into pRB16 using standard methods (18). Wild-type sequence for the C-terminal parts of these fragments was verified by sequencing with primers JB1052 (5'-CCATCCTCACCATCATCAC-3') (SEQ ID NO: 7) and JB1091 (5'-GCAGGGGAGGGAGAGATGG-3') (SEQ ID NO: 8). The hotspot mutations for codons 175 and 249 (in Table 3) were cloned into pRB16 using the same strategy. Phenotypes were checked as described above.

Forty one of the dominant-negative mutants had a single missense mutation and 8 had an in-frame deletion. Very strikingly, the mutations clustered around five of the six known hotspot codons in the TP53 gene: 245, 248, 249, 273 and 282 (1, 2, 4). We identified 5 mutations in codon 245, 2 in 248 and 2 in 273. 88% of the missense mutations hit the five hotspot regions for mutations (132–143, 151–159, 172–179, 237–249 and 272–286) or codons for which germline mutations have been described (FIG. 2) (2, 5, 7, 27, 28). 96% of the mutations we recovered in yeast have been described in human cancers or cancer cell lines (Table 3) (4, 29, 30). Our screen hit 5 of the 7 amino acids important in direct DNA binding (codons 241, 248, 273, 277 and 280) and 3 of the 4 amino acids involved in zinc atom contact (codons 176, 179 and 242) (31–33).

With the exception of H179N, all of the most dominant mutations (class 1) localized to codons 241–248 and 277–281. 83% of the mutations in these two regions had the class 1 phenotype (FIG. 2) indicating a strong correlation between the location of mutations and their degree of dominance.

TABLE 3

Sequence data on dominant-negative p53 mutations selected in yeast

| Mutation Number | Codon | Mutation Nucleotide | Amino Acid | Class | described in cancer (29, 30) |
|---|---|---|---|---|---|
| 32* | 127 | TCC->CCC | Ser->Pro | 2 | no |
| 27* | 132 | AAG->AAC | Lys->Asn | 2 | yes |
| 26* | 135 | TGC->TTC | Cys->Phe | 2 | yes |
| 43* | 151 | CCC->CGC | Pro->Arg | 2 | yes |

TABLE 3-continued

Sequence data on dominant-negative p53 mutations selected in yeast

| Mutation Number | Codon | Mutation Nucleotide | Amino Acid | Class | described in cancer (29, 30) |
|---|---|---|---|---|---|
| 67 | 151 | CCC->CAC | Pro->His | 2 | yes |
| 30* | 158 | CGC->CCC | Arg->Pro | 2 | yes |
| 76 | 176 | TGC->CGC | Cys->Arg | 2 | yes |
| 17* | 179 | CAT->AAT | His->Asn | 1 | yes |
| 50* | 236 | TAC->GAC | Tyr->Asp | 2 | yes |
| 64 | 241 | TCC->TTC | Ser->Phe | 1 | yes |
| 70 | 242 | TGC->TTC | Cys->Phe | 2 | yes |
| 13* | 244 | GGC->GAC | Gly->Asp | 1 | yes |
| 14* | 244 | GGC->AGC | Gly->Ser | 1 | yes |
| 12* | 245 | GGC->AGC | Gly->Ser | 1 | yes |
| 16* | 245 | GGC->CGC | Gly->Arg | 1 | yes |
| 55 | 245 | GGC->AGC | Gly->Ser | 1 | yes |
| 57 | 245 | GGC->AGC | Gly->Ser | 1 | yes |
| 101* | 245 | GGC->GAC | Gly->Asp | 1 | yes |
| 41* | 246 | ATG->ATT | Met->Ile | 2 | yes |
| 62 | 246 | ATG->AGG | Met->Arg | 1 | yes |
| 1* | 248 | CGG->TGG | Arg->Trp | 1 | yes |
| 63 | 248 | CGG->TGG | Arg->Trp | 1 | yes |
| 48* | 252 | CTC->ATC | Leu->Ile | 2 | no |
| 65 | 252 | CTC->ATC | Leu->Ile | 2 | no |
| 20* | 257 | CTG->CCG | Leu->Pro | 2 | yes |
| 37* | 257 | CTG->CAG | Leu->Gln | 2 | yes |
| 36* | 259 | GAC->TAC | Asp->Tyr | 2 | yes |
| 29* | 265 | CTG->CCG | Leu->Pro | 2 | yes |
| 69 | 273 | CGT->CCT | Arg->Pro | 2 | yes |
| 74 | 273 | CGT->CCT | Arg->Pro | 2 | yes |
| 7* | 277 | TGT->TAT | Cys->Tyr | 1 | yes |
| 28* | 278 | CCT->CAT | Pro->His | 2 | yes |
| 38* | 278 | CCT->TCT | Pro->Ser | 2 | yes |
| 10* | 279 | GGG->GAG | Gly->Glu | 1 | yes |
| 53 | 279 | GGG->GAG | Gly->Glu | 1 | yes |
| 61 | 279 | GGG->GAG | Gly->Glu | 1 | yes |
| 8* | 280 | AGA->ACA | Arg->Thr | 1 | yes |
| 58 | 280 | AGA->AGC | Arg->Ser | 1 | no |
| 3* | 281 | GAC->GGC | Asp->Gly | 1 | yes |
| 5* | 281 | GAC->TAC | Asp->Tyr | 1 | yes |
| 56 | 281 | GAC->GGC | Asp->Gly | 1 | yes |
| 18*, 68, 71, 72, 73, 75 | Δ175–180 (or 176–181 or 177–182)† | | | 2 | yes |
| 35* | Δ216 (or 217 or 218)‡ | | | 2 | yes |
| 42* | Δ252–254 (or 251–253)§ | | | | |
| 175¶ | CGC->CAC | Arg->His | | 2 | yes |
| 249¶ | AGG->AGT | Arg->Ser | | 1 | yes |

Bold clones were characterized further by cloning the mutation into wild-type ADH-p53 and rechecking the phenotypes.
*These dominant-negative mutations were obtained as false positives in a cDNA library screen.
†This deletion presumably arises frequently because of the direct repeat GCGCTGC present at codons 175–176 and 181–182.
‡deletion of one of three tandem GTG codons.
§Direct repeat of ATC flanks deleted nucleotides.
¶These hot spot mutations were cloned into wild-type ADH-p53 since our screen did not identify mutations of these codons.

To exclude that second mutations up- or downstream of the core domain contributed to the described phenotypes, we subcloned NcoI/StuI fragments (codons 159–347 encoding only the mutation of interest as confirmed by sequencing) into a wild-type ADH-p53 plasmid for the following mutants: C176R, D175–180, D217, G245D, R248W, R273P, P278S and D281Y. In all cases the same dominant-negative phenotype was reproduced (FIG. 1, Table 3).

Our screen hit 3 hotspot amino acids (codons 245, 248 and 273) but failed to identify mutations in the other 3 (codons 175, 249 and 282). These hotspots in human cancers are due in large part to methylation of the CpG dinucleotides present in codons 175 and 282 and exposure to aflatoxin $B_1$ for codon 249 (1–4, 8); neither situation applies to our yeast system. Two amino acid substitutions for these hotspots, R175H and R249S, were subcloned into wild-type ADH-p53 and shown to prevent UAS53::URA3 transcription. These mutants were also found to be dominant over wild-type (FIG. 1, Table 3).

Example 4: Protein Expression Levels of Dominant-Negative TP53 Mutants

Figure 3:
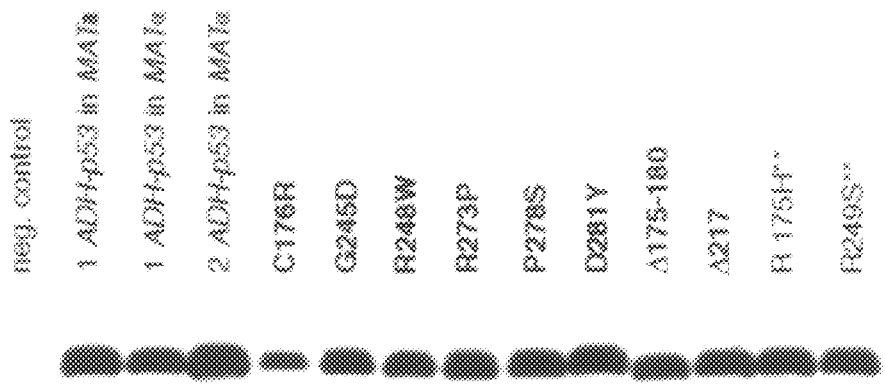
FIG. 3 Western Blot analysis with PAb 1801 (34) for p53 protein expression in yeast strains with wild-type and mutant ADH-p53 expression vectors. Protein levels for the dominant-negative mutants are similar to that of wild-type p53. The yeast strain with 2 expression vectors for wild-type ADH-p53 shows approximately two-fold more p53 protein than all other strains indicating that the strongest dominant p53 mutants of class 1 can in fact override higher levels of wild-type protein. For the p53 mutants in bold letters NcoI/StuI fragments with the mutations were cloned into wild-type ADH-p53. The mutants with ** represent hotspot codons which were not identified by our screen (1, 2, 4).

The wild-type and the mutant ADH-p53 genes are expressed from the same promoter in our system. In order to investigate whether the dominant-negative phenotypes were partially caused by an increased stability of the mutant protein we analyzed protein levels by immunoblotting with anti-p53 antibody PAb 1801 (34). FIG. 3 shows that protein levels for the mutant p53 proteins were similar to that of wild-type.

Example 5: Analysis of Recessive TP53 Mutants.

We also analyzed the more abundant recessive TP53 mutants. Since we considered the likelihood of non-missense mutations high, we immunoblotted protein extracts from the 67 independently obtained recessive TP53 mutants. None of these clones showed full-length protein. Four mutants expressed shorter proteins consistent with C-terminal truncation since PAb 1801 recognizes the N-terminus (34).

Conclusions

We have used the methods and strains described here to isolate and analyze TP53 mutations. Based on our work in yeast, where recessive TP53 mutations outnumbered dominant ones by about two to one, we believe that recessive TP53 mutations probably occur at a higher rate in human cells than dominant mutations, but that the recessive mutations are much less likely to lead to cancer (and therefore to be sequenced) since the remaining wild-type allele continues to exert its important functions. Our selection in yeast for dominant-negative TP53 mutations has identified a variety of missense mutations and in-frame deletions whose locations show a striking correlation with the hotspot regions of human cancer mutations. This suggests that the high frequency of human cancer mutations in these hotspot regions is in large part due to their dominant-negative effect on the wild-type p53 protein. Our data shows that the dominant negative mutants interfere with the wild-type protein to varying degrees, thus the amount of residual p53 activity in cells heterozygous for different TP53 mutations is likely to be different. However, even for the strongest dominant-negative mutants, there is likely to be some residual p53 function. The dominant-negative interference with the function of wild-type p53 should lead to elevated rates of DNA damage, chromosome loss, and other forms of loss of heterozygosity of the TP53 locus. Loss of heterozygosity would eliminate the residual activity provided by the wild-type TP53 allele and provide the (pre-)malignant clone with further growth advantages.

Class 1 p53 mutants in our assay are more proficient than class 2 mutants in interfering with wild-type p53 function. The locations of all class 1 mutations correspond closely to areas of the core domain which are essential for the structure of the DNA binding surface of p53 (L2 loop, codons 163–195 and L3 loop, codons 236–251), for major groove contacts in the pentamer sequence of the consensus DNA binding site (H2 a helix of the loop-sheet-helix motif, codons 278–286) and for minor groove contacts in the A T-rich region of the binding site (L3 loop) (31–33). These mutations may be more efficient in destabilizing a heterotetramer of mutant and wild-type p53. Assuming i) a single mutant subunit can poison a p53 tetramer, ii) equal size pools of mutant and wild-type protein and iii) unbiased mixing of mutant and wild-type subunits, heterozygous dominant mutations should lower p53 activity 16-fold. Thus, overexpression of a dominant-negative mutant relative to wild-type is theoretically not required for abrogation of wild-type p53 function, and our experiments in yeast confirm this. These data suggest that the mutant p53 overexpression observed in human cancers represents an additional level of complexity in p53 deregulation.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES CITED

1. Hollstein, M., Sidransky, D., Vogelstein, B. & Harris, C. C. (1991) Science 253, 49–53.
2. Caron de Fromentel, C. & Soussi, T. (1992) Genes Chromosom Cancer 4, 1–15.
3. Harris, C. C. & Hollstein, M. (1993) N Engl J Med 329, 1318–27.
4. Greenblatt, M. S., Bennett, W. P., Hollstein, M. & Harris, C. C. (1994) Cancer Res 54, 4855–78.
5. Nigro, J. M., Baker, S. J., Preisinger, A. C., Jessup, J. M., Hostetter, R., Cleary, K., Bigner, S. H., Davidson, N., Baylin, S., Devilee, P. & et al. (1989) Nature 342, 705–8.
6. Baker, S. J., Preisinger, A. C., Jessup, J. M., Paraskeva, C., Markowitz, S., Willson, J. K., Hamilton, S. & Vogelstein, B. (1990) Cancer Res 50, 7717–22.
7. Frebourg, T. & Friend, S. H. (1992) J Clin Invest 90, 1637–41.
8. Donehower, L. A. & Bradley, A. (1993) Biochim Biophys Acta 1155, 181–205.
9. Malkin, D. (1994) Annu Rev Genet 28, 443–65.
10. Michalovitz, D., Halevy, O. & Oren, M. (1991) J Cell Biochem 45, 22–9.
11. Vogelstein, B. & Kinzler, K. W. (1992) Cell 70, 523–6.
12. Zambetti, G. P. & Levine, A. J. (1993) Faseb J 7, 855–65.
13. Hann, B. C. L., D. P. (1995) Nature Genet. 9, 221–222.
14. Rose, M. D., Winston F., and Hieter P. (1990) Methods in yeast genetics: a laboratory course manual. (Cold Spring Harbor Laboratory, Cold Spring Harbor, N.Y.).
15. Ishioka, C., Frebourg, T., Yan, Y. X., Vidal, M., Friend, S. H., Schmidt, S. & Iggo, R. (1993) Nature Genet 5, 124–9.
16. Sikorski, R. S. & Hieter, P. (1989) Genetics 122, 19–27.
17. Devine, S. E. & Boeke, J. D. (1994) Nucleic Acids Res 22, 3765–72.
18. Sambrook, J., Fritsch, E. F., Maniatis, T. (1989) Molecular cloning. A laboratory manual. (Cold Spring Harbor Laboratory Press, Cold Spring Harbor, N.Y.).
19. Fields, S. & Song, O. (1989) Nature 340, 245–6.
20. Gyuris, J., Golemis, E., Chertkov, H. & Brent, R. (1993) Cell 75, 791–803.
21. Durfee, T., Becherer, K., Chen, P. L., Yeh, S. H., Yang, Y., Kilburn, A. E., Lee, W. H. & Elledge, S. J. (1993) Genes Dev 7, 555–69.
22. Wang, M. M. & Reed, R. R. (1993) Nature 364, 121–6.
23. Fields, S. & Jang, S. K. (1990) Science 249, 1046–9.
24. Boeke, J. D., LaCroute, F. & Fink, G. R. (1984) Mol Gen Genet 197, 345–6.

25. el-Deiry, W. S., Kern, S. E., Pietenpol, J. A., Kinzler, K. W. & Vogelstein, B. (1992) *Nature Genet* 1, 45–9.
26. Herskowitz, I. (1987) *Nature* 329, 219–22.
27. Mazoyer, S., Lalle, P., Moyret-Lalle, C., Marcais, C., Schraub, S., Frappaz, D., Sobol, H. & Ozturk, M. (1994) *Oncogene* 9, 1237–9.
28. Gutierrez, M. I., Bhatia, K. G., Barreiro, C., Spangler, G., Schvartzmann, E., Muriel, F. S. & Magrath, I. T. (1994) *Hum Mol Genet* 3, 2247–8.
29. Cariello, N. F., Beroud, C. & Soussi, T. (1994) *Nucleic Acids Res* 22, 3549–50.
30. Hollstein, M., Rice, K., Greenblatt, M. S., Soussi, T., Fuchs, R., Sorlie, T., Hovig, E., Smith-Sorensen, B., Montsano, R. & Harris, C. C. (1994) *Nucleic Acids Res* 22, 3551–5.
31. Cho, Y., Gorina, S., Jeffrey, P. D. & Pavletich, N. P. (1994) *Science* 265, 346–55.
32. Friend, S. (1994) *Science* 265, 334–5.
33. Prives, C. (1994) *Cell* 78, 543–6.
34. Banks, L., Matiashewski, G. & Crawford, L. (1986) *Eur J Biochem* 159, 529–34.

We claim:

1. A yeast cell comprising:

(a) a first reporter gene which is selectable or counterselectable, wherein the reporter gene is operably linked to a DNA sequence to which human p53 specifically binds; and (b) a first fusion gene which expresses a human p53 in the cell, the fusion gene comprising a promoter operably linked to a human p53 coding sequence.

2. The cell of claim 1 wherein the reporter gene is integrated into the genome of the cell.

3. The cell of claim 1 wherein the promoter is that of alcohol dehydrogenase.

4. The cell of claim 1 wherein the human p53 gene coding sequence is that of an allele found in a human tumor.

5. The cell of claim 1 wherein the human p53 gene coding sequence is that of a wild-type allele.

6. The cell of claim 1 wherein the human p53 gene coding sequence contains a mutation.

7. The cell of claim 1 wherein the human p53 gene coding sequence contains a dominant-negative mutation.

8. The cell of claim 1 wherein the reporter gene is selected from the group consisting of URA3, LYS2, LYS5, CAN1, MET2, MET15, and GAL1.

9. The cell of claim 6 further comprising:

a second fusion gene, wherein the second fusion gene expresses wild-type human p53 in the cell, the second fusion gene comprising a promoter operably linked to a human p53 coding sequence.

10. The cell of claim 6 further comprising:

a second reporter gene, wherein the second reporter gene is counterselectable, wherein the reporter gene is operably linked to a DNA sequence to which human p53 specifically binds.

11. The cell of claim 10 wherein the second reporter gene is the same as the first reporter gene.

12. A tripartite gene fusion of:

(a) a human p53-specific DNA-binding site;

(b) a yeast URA3 gene; and (c) a portion of a yeast SPO13 gene;

wherein the human p53-specific DNA-binding site is upstream of the URA3 gene, and wherein the portion of the yeast SPO13 gene is interposed between the URA3 gene and the human p53-specific DNA-binding site, and wherein the portion of the yeast SPO13 gene consists of the first 15 codons of SPO13 and nucleotides 5' to the coding sequence thereof.

* * * * *